(12) United States Patent
Ono et al.

(10) Patent No.: US 10,843,183 B2
(45) Date of Patent: Nov. 24, 2020

(54) ISOLATION DEVICE WITH BUILT-IN PARTICLE COUNTER

(71) Applicant: Hitachi Industrial Equipment Systems Co., Ltd., Tokyo (JP)

(72) Inventors: Keiichi Ono, Tainai (JP); Tomoyuki Suzuki, Tainai (JP)

(73) Assignee: Hitachi Industrial Equipment Systems Co., Ltd., Tokyo (JP)

( * ) Notice: Subject to any disclaimer, the term of this patent is extended or adjusted under 35 U.S.C. 154(b) by 176 days.

(21) Appl. No.: 16/309,337

(22) PCT Filed: May 12, 2017

(86) PCT No.: PCT/JP2017/017979
§ 371 (c)(1),
(2) Date: Dec. 12, 2018

(87) PCT Pub. No.: WO2018/047409
PCT Pub. Date: Mar. 15, 2018

(65) Prior Publication Data
US 2019/0310177 A1    Oct. 10, 2019

(30) Foreign Application Priority Data

Sep. 9, 2016  (JP) ................................. 2016-176659

(51) Int. Cl.
*B01L 1/00* (2006.01)
*B01L 1/02* (2006.01)
(Continued)

(52) U.S. Cl.
CPC ................. *B01L 1/00* (2013.01); *B01L 1/025* (2013.01); *B01L 1/04* (2013.01); *G01N 15/06* (2013.01); *G01N 33/0009* (2013.01)

(58) Field of Classification Search
CPC ... B01L 1/00; B01L 1/025; B01L 1/04; G01N 15/06; G01N 33/0009
See application file for complete search history.

(56) References Cited

U.S. PATENT DOCUMENTS

| 2003/0047012 A1* | 3/2003 | Storbeck | ................ | G01N 15/06 |
| | | | | 73/865.5 |
| 2008/0047373 A1* | 2/2008 | Ahn | .................... | G01N 15/0266 |
| | | | | 73/865.5 |

(Continued)

FOREIGN PATENT DOCUMENTS

| JP | 2000-93815 A | 4/2000 |
| JP | 2001-58114 A | 3/2001 |

(Continued)

OTHER PUBLICATIONS

International Search Report (PCT/ISA/210) issued in PCT Application No. PCT/JP2017/017979 dated Aug. 8, 2017 with English translation (five (5) pages).

(Continued)

*Primary Examiner* — David Z Huang
(74) *Attorney, Agent, or Firm* — Crowell & Moring LLP

(57) ABSTRACT

An isolation device for supplying a workspace with clean air resulting from dust filtration by an air cleaning means accurately manages the number of fine particles in a workspace and prevents fine particles from mixing with an experimental material. The isolation device includes a measurement probe; a particle counter for measuring the fine-particle counts for a plurality of particle sizes in the workspace air and outputting the measurements; a storage unit for storing, for each of the plurality of particle sizes and for work times and non-work times, management fine-particle counts at which the number of fine particles per unit volume is determined to be large; a cleanliness determination unit that compares the fine particle counts and the management fine-particle counts; and an output unit for outputting an alarm when the work-time/non-work time fine particle count for a particle size in the workspace exceeds the corresponding management fine-particle count.

5 Claims, 11 Drawing Sheets

(51) Int. Cl.
 *B01L 1/04* (2006.01)
 *G01N 15/06* (2006.01)
 *G01N 33/00* (2006.01)

(56) References Cited

U.S. PATENT DOCUMENTS

| | | | | |
|---|---|---|---|---|
| 2010/0045982 | A1* | 2/2010 | Tsuneta | G01N 15/14 |
| | | | | 356/338 |
| 2018/0001315 | A1* | 1/2018 | Kaneko | B01L 1/02 |
| 2018/0214861 | A1* | 8/2018 | Ono | F24F 3/161 |

FOREIGN PATENT DOCUMENTS

| | | |
|---|---|---|
| JP | 2005-279575 A | 10/2005 |
| JP | 2 01 5-1 21 5 | 7/2015 |
| JP | 2016-8933 A | 1/2016 |
| JP | 2016-105043 A | 6/2016 |
| WO | WO 2008/139777 A1 | 11/2008 |
| WO | WO 2016/079777 A1 | 5/2016 |

OTHER PUBLICATIONS

Japanese-language Written Opinion (PCT/ISA/237) issued in PCT Application No. PCT/JP2017/017979 dated Aug. 8, 2017 (three (3) pages).

* cited by examiner

F I G. 1A
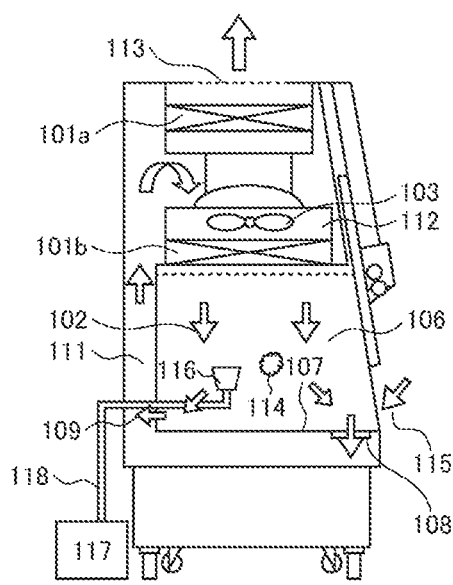
F I G. 1B
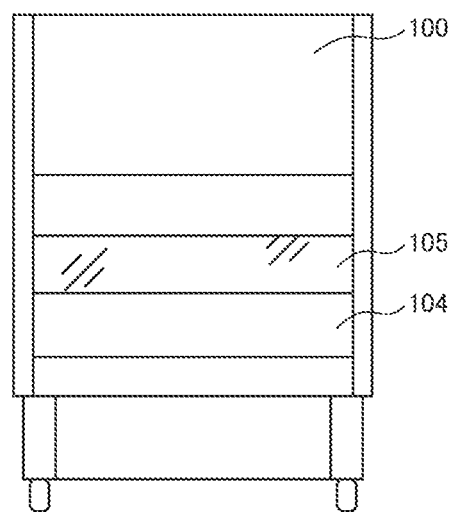

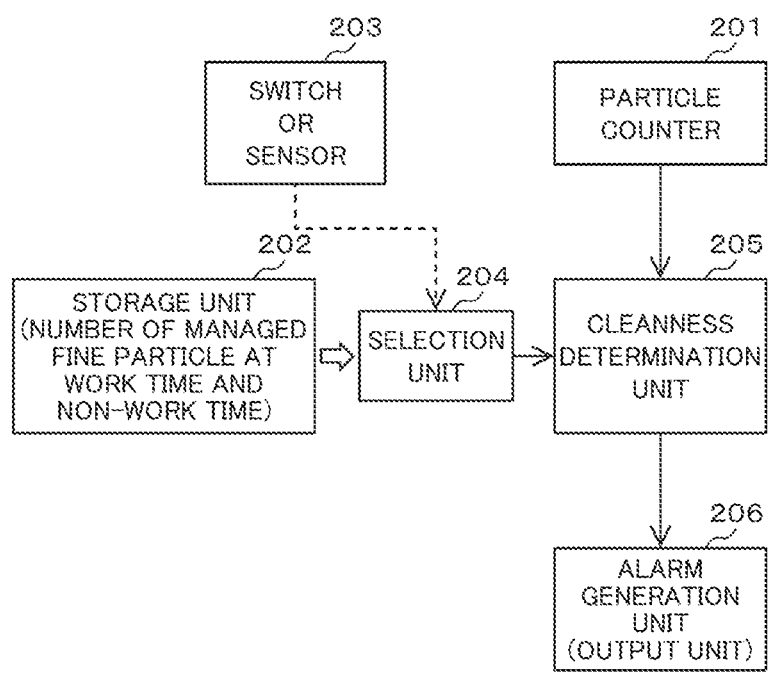
F I G. 3B

F I G. 5A
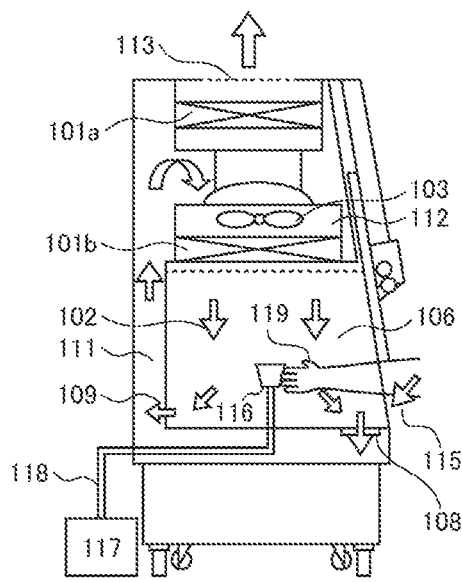
F I G. 5B
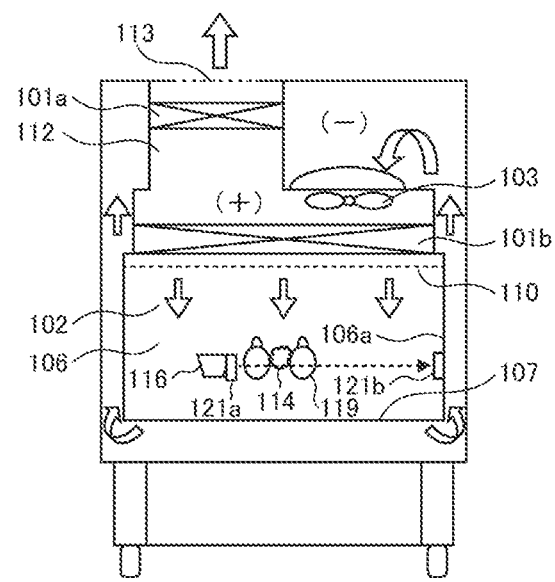

F I G. 6A
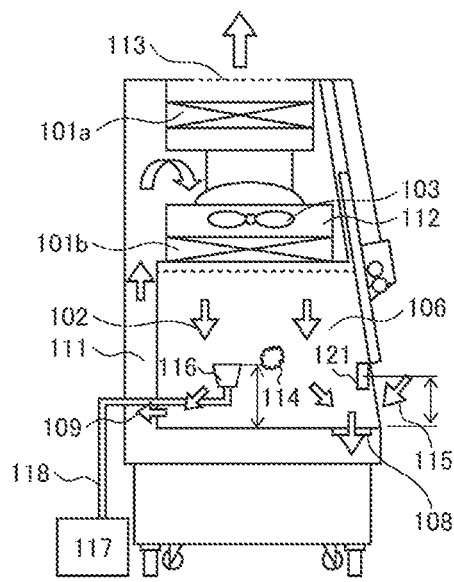
F I G. 6B
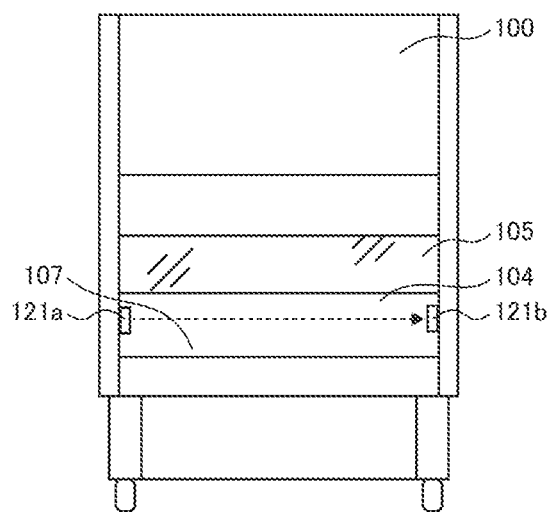

ISOLATION DEVICE WITH BUILT-IN PARTICLE COUNTER

TECHNICAL FIELD

The present invention relates to a technique for managing the number of fine particles in a workspace in an isolation device such as a safety cabinet, a clean bench (registered trademark), an isolator, and a clean booth used in an important zone at the time of producing a sterile medicinal product.

BACKGROUND ART

When producing the sterile medicinal products by an aseptic manipulation method, a class II cabinet for biohazard countermeasure (hereinafter referred to as a safety cabinet), a clean bench, an isolator, and a clean booth are used as important zones that manage sterility in the workspace. In the important zones, it is necessary to manage the number of microorganisms and the number of fine particles. In a vertical flow clean bench, when cleaned air from which fine particles are removed is supplied into the workspace from an upper part of the workspace and the cleaned air is blown out from a working opening portion on a front surface, the fine particles are prevented from entering the workspace, while maintaining the inside of the workspace at a positive pressure. Since the air in the workspace comes down to a researcher who uses the clean bench, the air cannot be used when the sample to be handled is infectious. The same also applies to the clean booth.

The safety cabinet supplies the cleaned air from which the fine particles are removed into the workspace from the upper part of the workspace, and the air in the workspace is dividedly sucked into a workbench front suction port formed under the working opening portion on the front surface and a rear suction port formed on a rear surface of the workspace. The workbench front suction port sucks air of a laboratory air in which the safety cabinet is placed, and forms an inflow air flow. Since the inside of the workspace and the air in the laboratory in which the safety cabinet is placed are shut off by the inflow air flow, samples to be handled inside the workspace of the safety cabinet is prevented from leaking out of the safety cabinet. Although the researcher faces the working opening portion on both the clean bench and the safety cabinet, since the experimental material of the internal biological material of the safety cabinet does not leak out, in many cases, the safety cabinet is used for the producing and researching of sterile medicinal product. An isolator supplies the cleaned air from which fine particles are removed into the workspace from the upper part of the workspace, and the air is exhausted to the outside of the isolator from an exhaust port formed under the workspace. The researcher inserts his hand into a glove formed in the isolator and conducts experiments in the workspace through the glove. By removing the fine particulates contained in the air to be exhausted with a HEPA filter or the like, it is possible to prevent the fine particles of the experimental material used inside the isolator from leaking to the outside of the isolator. When producing the sterile medicinal product, in all of the clean bench, the safety cabinet, the isolator, and the clean booth, the number of fine particles per unit volume of the workspace needs to be managed to a specified value or less. When there is the number or more of managed fine particles, the manufactured medicinal product becomes defective.

As a background technique in this technical field, there is JP 2005-279575 A (Patent Document 1). Patent Document 1 discloses a method of measuring the number of fine particles in the workspace in units of microns or less, by providing a suction portion for sucking air in the workspace of the clean bench or the safety cabinet on a wall surface of the workspace and by connecting the suction portion and a cleanliness sensor. Further, Patent Document 1 discloses a method of executing a predetermined alarm operation when the cleanness falls below a prescribed value. It is possible to manage the number of fine particles in the workspace during working of the clean bench or the safety cabinet, using the method.

CITATION LIST

Patent Document

Patent Document 1: JP 2005-279575 A

SUMMARY OF THE INVENTION

Problems to be Solved by the Invention

When using the cleanliness sensor of the workspace of the clean bench or the safety cabinet of Patent Document 1, it is possible to measure and manage the number of fine particles in the workspace. The cleanliness is a level of the number of fine particles present per unit volume. However, Patent Document 1 does not disclose a specific size of the number of fine particles to be managed. As an example of managing the number of fine particles in the workspace, there is a "guideline on producing of sterile medicinal products by aseptic manipulation" by the Ministry of Health, Labor and Welfare as administrated notice dated Apr. 20, 2011 (H23). In the guideline, a maximum permissible number of fine particles of the operation place of the product relating to sterile medicinal products in the important zone is 3,520 (pieces/m$^3$) with a fine particle size of 0.5 μm or more at the time of non-work and at the time of work. The number corresponds to class 5 (ISO 5 of ISO 14644-1) of JIS B 9920 "evaluation method of air cleanliness of clean room". In addition, the number of floating fine particles with a particle size of 5.0 μm or more is periodically measured and trend analysis thereof is performed, and the fine particles with the particle size of 5.0 μm or more are not necessarily managed at all times. At the time of work, the number of fine particles generated in the operation place by the experiment of the worker is the target, and at the time of non-work, since generation of fine particles in the operation place is extremely small, the number of fine particles leaking from the HEPA filter that supplies the cleaned air to the operation place is the target. In the guideline, the maximum allowable number of fine particles is set to 3,520 (pieces/m$^3$) with the fine particle size of 0.5 μm or more at the time of non-work and at the time of work. However, in the space of a maximum of 3,520 (pieces/m$^3$) at the time of non-work, even if the fine particles are generated by the operation, it is unlikely that the number of generated fine particles reaches the same number of up to 3,520 (pieces/m$^3$). At the time of non-work, it should be smaller numbers.

As for an upper limit concentration of cleanliness class 5, as shown in Table 1, in addition to particles of 0.5 μm or more, particles of 0.3 μm or more, particles of 1.0 μm or more, and the like are also defined. However, a generation ratio of each fine particle size in the workspace is not the same as a ratio of the upper limit concentration of cleanliness class 5. For example, even if the number of fine particles having a fine particle size of 0.5 μm or more is measured and managed at all times, when general bacteria are scattered in the workspace from worker with large amounts of general bacteria attached to their hands by 1.0 μm or more, although the number of fine particles of 0.5 μm or more satisfies the cleanliness class 5, there is a possibility that the number of fine particles of 1.0 μm or more may not satisfy the cleanliness class 5. In this case, a larger amount of general bacteria than the upper limit concentration of cleanliness class 5 will be mixed during manufacture of the sterile medicinal product.

TABLE 1

Upper limit concentration of cleanliness class 5 of JIS B 9920 "Evaluation method of air cleanliness of clean room"

| | Upper limit concentration (pieces/m³) Measurement particle size | | | | | |
|---|---|---|---|---|---|---|
| Cleanliness class | 0.1 μm or more | 0.2 μm or more | 0.3 μm or more | 0.5 μm or more | 1 μm or more | 5 μm or more |
| Class 5 | 100,000 | 23,700 | 10,200 | 3,520 | 832 | 29 |

An object of the present invention is to precisely manage the number of fine particles in the workspace and to prevent fine particles from mixing into the experimental material.

Solutions to Problems

An example of the "isolation device with built-in particle counter" of the present invention for solving the above-mentioned problem is an isolation device which supplies cleaned air with dust filtered by air cleaning means to a workspace, the isolation device including:

a measurement probe for air intake disposed in the workspace;

a particle counter which measures and outputs the number of fine particles having a plurality of particle sizes of air in the workspace taken in by the measurement probe;

a storage unit which stores the number of managed fine particles for each of a plurality of particle sizes, the number of managed fine particles being determined to be large in number of fine particles per unit volume, by being divided into a work time and a non-work time;

a cleanliness determination unit which compares the number of fine particles having a plurality of particle sizes measured by the particle counter with the number of managed fine particles having a plurality of particle sizes stored in the storage unit to determine cleanliness; and an output unit which outputs an alarm when the number of fine particles in the workspace during operation is determined to be greater than the number of the managed fine particles for any of the particle size, and for each of the work time or the non-work time in the cleanliness determination unit.

Effects of the Invention

According to the present invention, it is possible to precisely manage the number of fine particles in a workspace, and to prevent fine particles from mixing into experimental materials.

BRIEF DESCRIPTION OF THE DRAWINGS

FIG. 1A is a side sectional structural view illustrating a safety cabinet according to a first embodiment of the present invention.

FIG. 1B is an example of an external front view illustrating the safety cabinet of the first embodiment.

FIG. 3B is an example of a block diagram of a cleanliness determination device of the safety cabinet according to the first embodiment.

FIG. 5A is an example of a side sectional structural view illustrating a safety cabinet during working of a third embodiment of the present invention.

FIG. 5B is an example of a cross-sectional front view illustrating the safety cabinet during working of the third embodiment.

FIG. 6A is a side sectional structural view illustrating a safety cabinet according to a fourth embodiment of the present invention.

FIG. 6B is an example of an external front view illustrating the safety cabinet of the fourth embodiment.

MODES FOR CARRYING OUT THE INVENTION

Figure 2A:
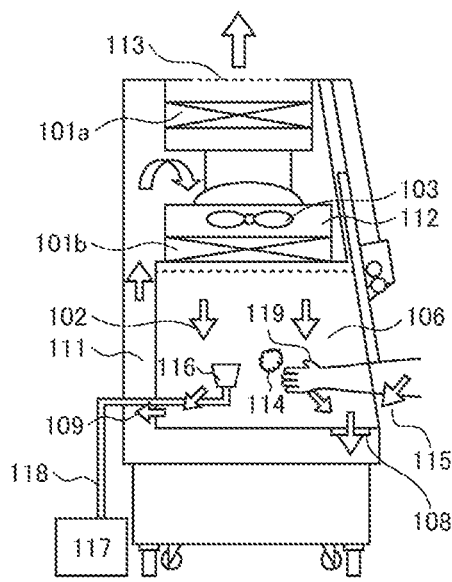
FIG. 2A is an example of a side sectional structural view illustrating the safety cabinet during working of the first embodiment.

Hereinafter, embodiments of the present invention will be described with reference to the drawings. In each drawing for describing the embodiments, the same constituent elements are denoted by the same names and reference numerals, and the repetitive description thereof will not be provided.

First Embodiment

FIGS. 1A to 3B illustrate a safety cabinet according to a first embodiment of the present invention. FIG. 1A is a side sectional structural view illustrating the safety cabinet of the first embodiment, and FIG. 1B is an example of an external front view illustrating the safety cabinet of the first embodiment. Further, FIG. 2A is a side sectional structural view illustrating the safety cabinet during the operation of the first embodiment, and FIG. 2B is an example of a cross-sectional front view illustrating the safety cabinet during the operation of the first embodiment.

At the time of work of the safety cabinet 100, a blower 103 operates to pressurize a pressure chamber 112. A blowing HEPA filter 101b and an exhaust HEPA filter 101a are connected to the pressure chamber 112. As the pressure chamber 112 is pressurized, dust is removed from the air in the pressure chamber 112 by the blowing HEPA filter 101b and, the air is supplied into the workspace 106 as cleaned air 102. A rectifying plate 110 is disposed right under the blowing HEPA filter 101b in the upper part of the workspace 106. The wind speed blown out as the cleaned air 102 is made uniform by the rectifying plate 110. The fact that the wind speed blown out from the rectifying plate 110 is uniform means that the movement of the air flow in a direction parallel to the surface of the rectifying plate 110 is the minimum.

The cleaned air 102 blown into the workspace 106 descends in the workspace 106, a part thereof is sucked into a rear suction port 109, and the other part thereof is sucked into a workbench front suction port 108. When sucking air from the workbench front suction port 108, an inflow air flow 115 is simultaneously generated in a working opening portion 104, and air outside the safety cabinet 100 is also sucked together. When the cleaned air 102 is dividedly sucked into the rear suction port 109 and the workbench front suction port 108, the uniformity of the wind speed is maintained up to the vicinity of the workbench 107 on the lower surface of the workspace 106. Further, the air in the workspace 106 and the outside of the safety cabinet 100 are physically isolated from each other by the inflow air flow 115 sucked into the workbench front suction port 108 in the lower part of the working opening portion 104. Because of a physical isolation, the dust containing general bacteria contained in the air outside the safety cabinet 100 does not contaminate the inside of the workspace 106, and the dust 114 containing the aerosol and the bacteria handled in the workspace 106 does not leak out of the safety cabinet 100 through the working opening portion 104.

The air sucked in from the workbench front suction port 108 and the rear suction port 109 passes through the lower part of the workbench 107 and a rear flow path 111 and is sucked into the blower 103 to pressurize the pressure chamber 112. Dust is again removed from the air in the pressure chamber 112 by the blowing HEPA filter 101b and, the air is supplied as the cleaned air 102 into the workspace 106. Further, the dust 114 containing aerosol and bacteria is removed from other air by the exhaust HEPA filter 101a, and other air is exhausted to the outside of the safety cabinet 100 from the exhaust port 113.

The worker inserts his hand 119 from the working opening portion 104 into the workspace 106 to perform the experiment operation. The worker looks into the workspace 106 from a front shutter 105 made of tempered glass or the like. The main purpose of using the safety cabinet 100 is to handle pathogens and the like in the workspace 106 and to prevent the experimenter from being infected with the pathogens and the like. Recently, dust, general bacteria and the like outside the safety cabinet 100 do not enter the workspace 106, while maintaining the clean state in which the cleaned air 102 is supplied to the workspace 106 of the safety cabinet 100. Thus, in some cases, the safety cabinet may be used for aseptic manipulation when producing the sterile medicinal product. When producing the sterile medicinal product, it is not possible for unnecessary bacteria to be contained in chemicals to be administered to humans. Therefore, the state in which the number of fine particles in the workspace 106 is smaller than the predetermined value is managed. In the above-mentioned "guidelines on the manufacture of sterile medicinal products by aseptic manipulation", the number of fine particles is set to be less than or equal to the number of fine particles in the environment of cleanliness class 5 in the important zone. In Japanese Pharmacopoeia (Notification No. 65 of the Ministry of Health, Labor and Welfare) which summarizes the method of producing chemicals, the air cleanliness for the manufacture of sterile medicinal products is similarly classified as grade A (a laminar flow operation zone), and at the time of non-work and at the time of work, the particle size is set as 0.5 μm or more and the maximum allowable number of fine particle is set as 3,520 pieces/m$^3$. The number corresponds to class 5 shown in Table 1. In order to manage the number of fine particles (pieces/m$^3$) of the space, a "light scattering type airborne particle counter" specified in JIS B 9921 (hereinafter referred to as a particle counter) is used.

When measuring the number of fine particles in the workspace 106, a measurement probe 116 is placed in the workspace 106. The measurement probe 116 is connected to a particle counter 117 by a sampling tube 118. When the particle counter 117 sucks air of a predetermined air volume per unit time, the air in the workspace 106 is taken in from the measurement probe 116 via the sampling tube 118. The particle counter 117 may count the number of fine particles in the taken air. The particle counter 117 may be disposed in the workspace 106 or may be disposed outside the workspace 106. When the particle counter 117 is disposed outside the workspace 106, the sampling tube 118 penetrates the workspace 106 and the wall surface of the safety cabinet 100. The suction port of the measurement probe 116 is disposed to face the direction in which the cleaned air 102 of the workspace 106 is blown out. When the flowing direction of the cleaned air 102 is different from the direction in which the measurement probe 116 sucks the air, there is a possibility that the measurement probe 116 cannot suck the dust 114 contained in the cleaned air 102.

Further, even if the direction in which the cleaned air 102 blows out and the direction in which the measurement probe 116 sucks the air are opposite to each other, when the speed at which the cleaned air 102 blows out is higher than the sucking speed of the measurement probe 116, there is a possibility that the dust 114 contained in the cleaned air 102 is not sucked by the measurement probe 116 and leaks out of the measurement probe 116, the measurement may not be performed correctly, and the measurement sensitivity may be lowered. In contrast, when the speed at which the cleaned air 102 blows out is slower than the sucking speed of the measurement probe 116, there is a possibility that the measurement probe 116 simultaneously sucks the surrounding cleaned air 102 not containing the dust 114, and as the concentration of the dust 114 decreases, the measurement sensitivity may be lowered. Therefore, as the blowing speed of the cleaned air 102 and the sucking speed of the measurement probe 116 become closer to each other, the measurement sensitivity becomes better. Since there are some wind speed distributions in the blowing wind speed of the cleaned air 102, it is difficult to match them in practice. Ideally, the difference between the blowing speed of the cleaned air 102 and the sucking speed of the measurement probe 116 is within +20%.

In the clean bench described in Patent Document 1, a suction portion for sucking air in the workspace is provided on the wall surface of the workspace. JIS B 9922 of the clean bench standard discloses that the constant speed suction is preferable when measuring the cleanliness which is the number of fine particles per unit volume. The constant speed suction means that the wind speed blown to the suction portion at the time of measurement is equal to the wind speed sucked from the suction portion. The difference between the blowing speed and the sucking speed influences the sensitivity of measurement of the number of fine particles. JIS B 9917-3: 2009 "clean room and attached clean environment" Part 3: Annex JA of the test method discloses that constant speed suction is desirably within ±20%. In Patent Document 1, the method of the air blown into the workspace of the clean bench and the method of the air sucked by the suction portion of the wall surface is a right angle direction and the constant speed suction is not established.

The clean bench standard JIS B 9922 discloses that the wind speed at the individual measurement points of the blowing wind speed of the clean bench of one-way flow is within ±20% with respect to an average wind speed. In the safety cabinet standard JIS K 3800 which does not regard the cleanliness as the performance requirement, the measured value at each point of the blowing wind speed is also described as being within ±20% of the average blowing wind speed. In the case of the safety cabinet, as a cross contamination prevention function between samples of the air flow balance test, a test method of proving that movement of air flow in a direction perpendicular to the blowing direction is minimal is defined. This means that uni-directionality (laminar flow) of the blowing wind speed is necessary to maintain the cleanliness of about class 5. When the blowing wind speed is in one direction, the movement of the air flow in the lateral direction perpendicular to the blowing direction is minimized. When the movement of the air flow in the direction perpendicular to the blowing direction is the minimum, if the suction portion for sucking the fine particles and the place where the fine particles to be managed generate are spaced apart in the direction perpendicular to the blowing direction, the suction portion does not suck the generated fine particles.

Next, in this embodiment, at the time of work, the hand 119 is inserted into the workspace 106 from the working opening portion 104 to handle the sterile medicinal product. The dust 114 containing aerosol that may occur in the producing process of sterile medicinal products and the dust 114 containing bacteria that may adhere to the hand 119 or the experimental instrument may be scattered inside the workspace 104 due to the movement of the hand 119. The number of fine particles of the dust 114 per unit volume is set to 3,520 pieces/m$^3$ at the particles of 0.5 µm or more, as a maximum allowable number of fine particles at the time of work in the guideline or the like.

The upper limit concentration of cleanliness class 5 of JIS B 9920 "evaluation method of air cleanliness of clean room" is the upper limit concentration of fine particles (pieces/m$^3$) with each particle size of 0.1 µm or more to 5 µm or more. The number of the upper limit concentration is different for each particle size. A generation ratio for each particle size of the dust 114 generated in the workspace 106 at the time of work may be different from a generation ratio of each particle size of the upper limit concentration of the cleanliness class 5 of JIS B 9920. For example, when the concentration of particles generated from 0.5 µm or more to less than 1.0 µm is small and the concentration of particles generated of 1.0 µm or more is large, the particle concentration of 0.5 µm or more satisfies the class 5, but the particle concentration of 1.0 µm or more may not satisfy class 5 in some cases. This means that there is a possibility that a large amount of fine particles of 1.0 µm or more will be contaminated at the time of producing a sterile medicinal product. Therefore, it is necessary to measure and manage not only the particle size of 0.5 µm or more but also a plurality of particle sizes such as 1.0 µm or more.

At the time of non-work, the safety cabinet 100 is operated in a state in which the hand 119 is not inserted in the workspace 106. The safety cabinet 100 has a working opening portion 104. In the producing environment of sterile medicinal products, in terms of the risk management in which air of an laboratory with the safety cabinet 100 disposed therein enters from the working opening portion 104, the safety cabinet is disposed in the environment in which the number of particles of 0.5 µm or more is 352,000 pieces/m$^3$ at the time of non-work. The transmittance of the HEPA filter 101 used for the safety cabinet 100 is assumed that there is no part exceeding 0.01% at 0.3 µm particles. It is considered that 0.3 µm is a particle size that is difficult for the HEPA filter 101 to collect. For example, when the transmittance of the HEPA filter 101 is 0.01% even with a particle size of 0.5 µm, even if the particle concentration of the cleaned air 102 blown into the workspace 106 of the safety cabinet 100 is simply calculated, particle concentration of 0.5 µm particles of the laboratory is 352,000 pieces/m$^3$×0.01%=35.2 pieces/m$^3$. 35.2 pieces/m$^3$ is the number of 1/100 of 3,520 pieces/m$^3$ pieces managed by class 5. This means that, even if the hole opens in the HEPA filter 101 and the transmittance rises from 0.01% to 0.1%, the fine particle concentration in the workspace 106 satisfies 3,520 pieces/m$^3$ in class 5. Furthermore, when the blowing wind speed of the cleaned air 102 is unidirectional (laminar flow), since there is little possibility that the dust 114 moves in a direction perpendicular to the blowing wind speed on the air flow at the time of non-work, there is a possibility that the fine particle concentration does not rise except in the vicinity of the place in which the hole of the HEPA filter 101 opens.

In order to solve this problem, the concentration of fine particles to be managed is divided between the work time and the non-work time.

Figure 3A:
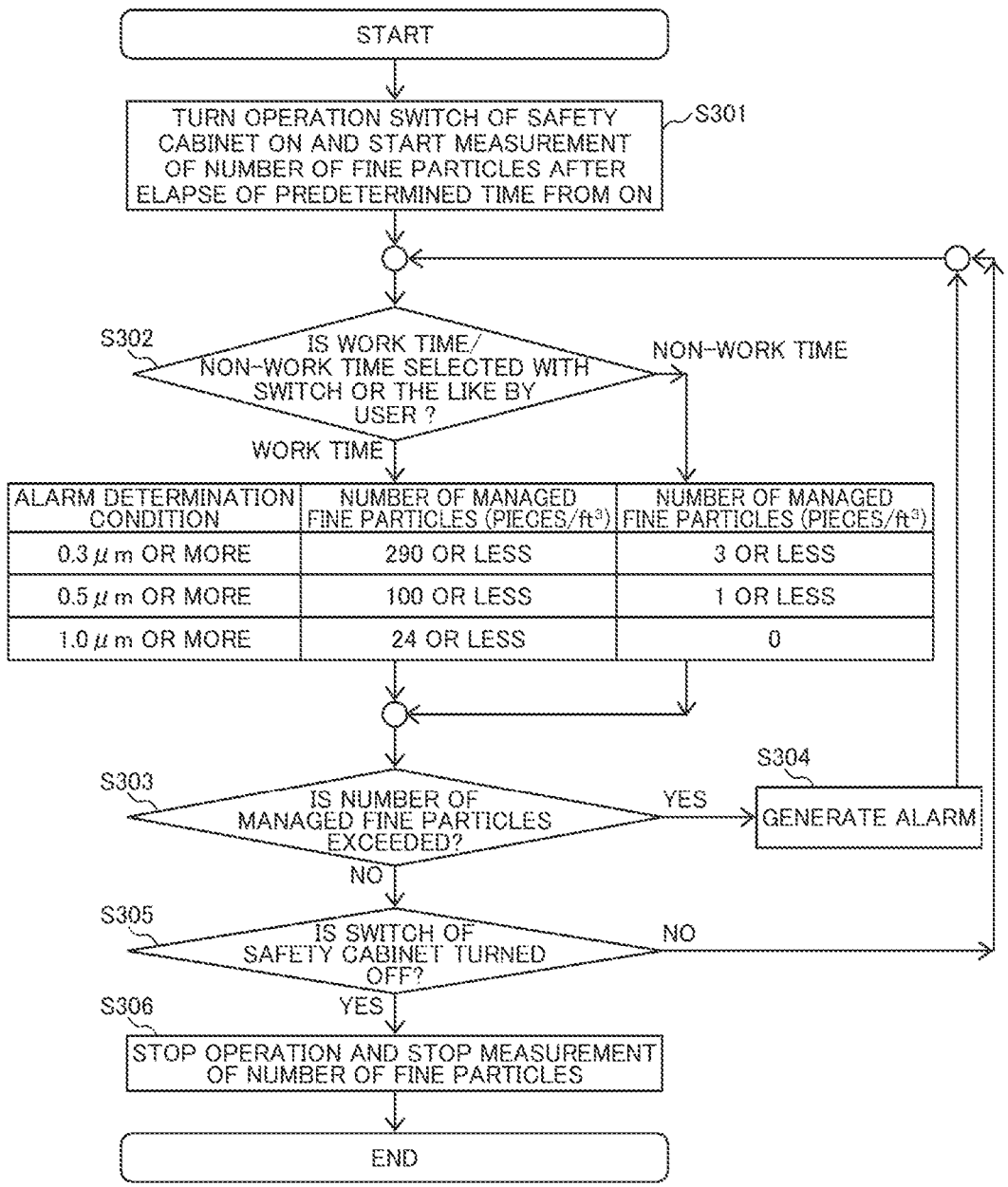
FIG. 3A is an example of an operational flowchart of the safety cabinet of the first embodiment.

FIG. 3A illustrates an example of an operational flowchart of the safety cabinet of the first embodiment.

The operation switch of the safety cabinet is turned on. The cleaned air 102 blows out into the workspace 106 of the safety cabinet 100 and the concentration of the fine particles in the workspace 106 decreases. However, since the fine particle concentration does not decrease immediately after the operation switch of the safety cabinet is turned on, measurement of the number of fine particles using the particle counter 117 is started after a predetermined time elapses from on (S301).

The user selects the work time or the non-work time with a switch or the like provided on the safety cabinet 100 or the particle counter 117 (S302). An example of the number of fine particles (pieces/ft$^3$) to be managed in the workspace 106 is illustrated in the flowchart of FIG. 3A. Here, the reason why the unit of the number of fine particles changes from (pieces/m$^3$) to (pieces/ft$^3$) is that the sucking speed of the commercially available particle counter is mainly the device of 1 ft$^3$/min (28.3 l/min) and 0.1 ft$^3$/min (2.83 l/min). Three kinds of determination conditions for warning when the concentration rises are 0.3 µm or more, 0.5 µm or more, and 1.0 µm or more. In JIS B 9920 "evaluation method of air cleanliness of clean room", as shown in Table 1, since six types are described from 0.1 µm or more to 5 µm or more, if there are plural particle sizes, it can be any number of two or six kinds. It is necessary to match with the decomposing ability of the particle counter to be used. The conditions for determining alarms have upper limit values of the different number of fine particles (pieces/ft$^3$) at the time of work and at the time of non-work.

In the first embodiment, at the time of work, the number of particles of 0.3 µm or more is managed to 290 or less (pieces/ft³), the number of particles of 0.5 µm or more is managed to 100 or less (pieces/ft³), and the number of particles of 1.0 µm or more is managed to 24 or less (pieces/ft³). The numbers are numbers obtained by converting the upper limit concentration (pieces/m³) of each fine particle size of cleanliness class 5 into the unit of pieces/ft³. Considering the safety factor, the numbers may be set to a number different from the above numbers by the user. When the above conditions are not satisfied (S303), an alarm is issued (S304). The alarm may be sound, display, command to a host device, or the like.

When the alarm is issued by the warning at the time of work, it is a case where the worker performs an inappropriate experimental work and a large amount of the dust 114 is generated. As the alarm is issued, the worker temporarily stops the operation while inserting the hand 119 into the workspace 106 due to the inappropriate work, thereby suppressing the generation of the dust 114. Drawing-out of the hand 119 suddenly from the workspace 106 is not carried out because it will bring the dust 114 containing bacteria from the workspace 106. Since the cleaned air 102 is constantly supplied to the workspace 106 from the upper side, the dust 114 at the alarm level is eliminated by the cleaned air 102, the dust 114 which is the number of fine particles is removed from the workspace 106, and the alarm is released. Experimental materials dealt with at the time of alarm are excluded because there is a possibility that unexpected fine particles may be mixed in, and the worker improves inappropriate manipulation procedure warned by alarm.

At the time of non-work, no dust 114 is generated in the workspace 106, and only the dust 114 leaking out of the blowing HEPA filter 101b has a possibility of entering the workspace 106. Therefore, the number of fine particles to be managed at the time of non-work is reduced than that at the time of work. In the first embodiment, one hundredth of the number of the managed fine particles at the work time is the number of the managed fine particles at the time of non-work. The number may be set by a user to a number different from the above number. In the case of increasing the number, it is not considered to increase the number at the time of non-work than the number at the time of work, from the viewpoint of the management.

At the time of non-work, when this condition is not satisfied (S303), alarm is issued by warning (S304), which means a possibility of breakage of the blowing HEPA filter 101b. Since the alarm at the time of non-work is caused by the device rather than the worker's experimental method, it is necessary to inspect the device.

When the number of fine particles measured by the particle counter 117 does not reach the number of managed fine particles (pieces/ft³), alarm is not issued by warning. Regardless of presence or absence of alarm of warning, the upper limit of the number of managed fine particles is determined during working of the safety cabinet 100.

When stopping the operation of the safety cabinet 100, the operation of the safety cabinet is stopped by turning the switch of the safety cabinet off (S305), and the measurement of the number of fine particles is also stopped (S306). After turning the switch off, the measurement of the number of fine particles may be first stopped, and the operation of the safety cabinet may be stopped after elapse of a predetermined time.

FIG. 3B illustrates a block configuration diagram of the cleanliness determining device for executing the operation flowchart of FIG. 3A.

A particle counter 201 corresponds to the particle counter 117 of FIG. 1A, and measures and outputs the number of fine particles having a plurality of particle sizes from the air in the workspace taken in by the measurement probe. A storage unit 202 stores the number of managed fine particles (managed concentration) at the time of work and at the time of non-work, and outputs the stored number of managed fine particles to a selection unit 204. The selection unit 204 selects the number of the managed fine particles at the time of work and the number of the managed fine particles at the time of non-work, depending on the work time or the non-work time, and outputs the number of the managed fine particles to a cleanliness determination unit 205. Switching between the work time and the non-work time is performed by the switch or output from a sensor 203. The switch is for the user to manually switch between the work time and the non-work time. Further, the sensor detects the work time and the non-work time, by detecting user's hand or the like as described in the second embodiment and the like.

The cleanliness determination unit 205 compares the number of managed fine particles at the time of work or the non-work which is input from the selection unit 204 with the number of fine particles measured by the particle counter 201 for each particle size, and gives an output if the number of measured fine particles exceeds the number of managed fine particles. An alarm generation unit 206, which is an output unit, for example, issues the alarm in accordance with the output of the cleanliness determination unit 205.

According to the present embodiment, a plurality of target particle sizes for counting the number of fine particles in the air containing fine particles taken in from the measurement probe is provided, the number of managed fine particles is provided for each target particle size, and the number of managed fine particles is provided in different numerical values for each of the work time at which the experiment is performed in the safety cabinet and for the non-work time at which only the safety cabinet is in operation, and an alarm is issued by the warning when exceeding the number of the managed fine particles. Therefore, the number of fine particles in the workspace is precisely managed, and the fine particles are prevented from mixing in the experimental material.

Second Embodiment

Figure 4A:
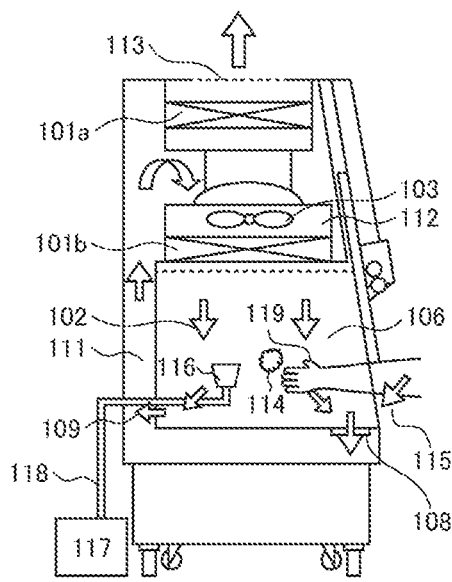
FIG. 4A is an example of a side sectional structural view illustrating a safety cabinet during working of a second embodiment of the present invention.
Figure 4B:
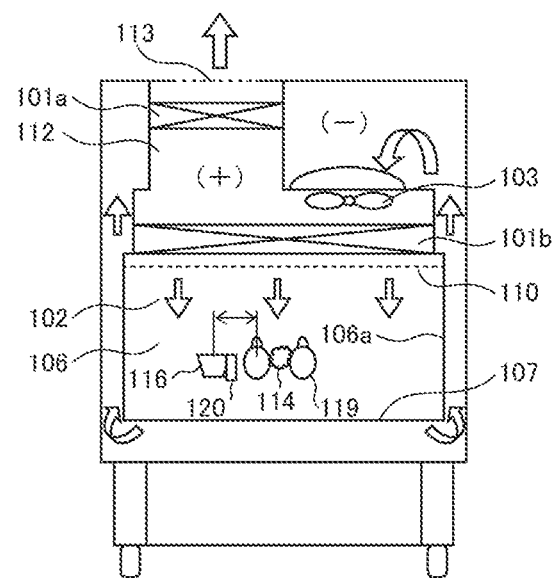
FIG. 4B is an example of a cross-sectional front view illustrating the safety cabinet during working of the second embodiment.

FIGS. 4A and 4B illustrate a safety cabinet according to a second embodiment of the present invention. FIG. 4A is a side sectional structural view illustrating the safety cabinet during working of the second embodiment, and FIG. 4B is an example of a cross-sectional front view illustrating the safety cabinet during working of the second embodiment.

Figure 2B:
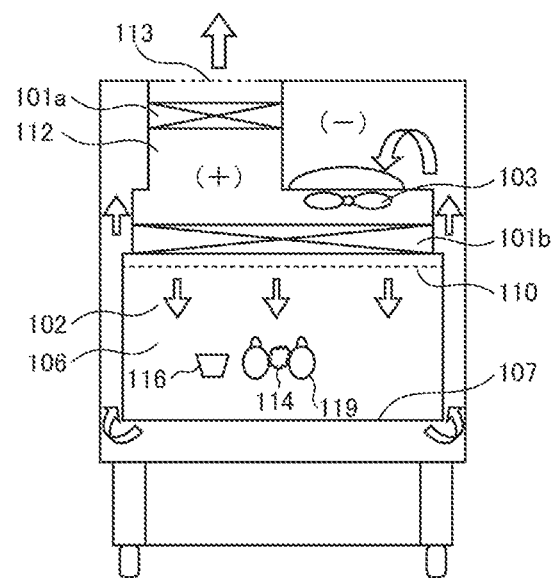
FIG. 2B is an example of a cross-sectional front view illustrating the safety cabinet during working of the first embodiment.

In the second embodiment, a proximity sensor 120 is provided in the measurement probe 116 in comparison with FIGS. 2A and 2B of the first embodiment.

Since the cleaned air 102 blown out of the rectifying plate 110 on the upper part of the workspace 106 of the safety cabinet 100 is unidirectional (laminar flow), the movement of air in a lateral direction perpendicular to the blowing direction is minimized. When approaching the workbench 107 due to the suction air flow of the rear suction port 109 and the workbench front suction port 108, an air flow divided into the rear side and the front side of the workspace 106 is generated. The rear suction port 109 and the workbench front suction port 108 form a suction port with substantially the same lateral dimension as the working opening portion 104 in parallel with the working opening portion 104. Therefore, the cleaned air 102 blows down to the vicinity of the workbench 107 with minimum movement of air in the lateral direction.

At the time of work, the dust 114 is generated from the vicinity of the hand 119 with which the user performs works. The generated dust 114 does not instantaneously spread all over the workspace 106. Therefore, if a distance between the hand 119 performing the working and the measurement probe 116 measuring the fine particles in the workspace 106 is far apart, there is a possibility that the measurement probe 116 does not take in the dust 114 during the work. In the second embodiment, the proximity sensor 120 is provided in the measurement probe 116, and a case in which the proximity sensor 120 reacts with the hand 119 is determined to be the work time.

Since the degree of movement of the air flow in the lateral direction with respect to the blowing direction varies depending on the amount of scattering of the dust 114 generated due to the working content of the user and the value of the blown wind speed of the cleaned air 102, the specific number of the distance at which the proximity sensor 120 reacts with the hand 119 is not provided. The distance can be set as appropriate by the user.

It should be noted that the proximity sensor 120 may be disposed on the wall surface of the workspace 106 instead of the measurement probe 116.

According to the present embodiment, since the proximity sensor is provided, it is possible to detect whether the user performs the work and detect the work time or the non-work time.

Third Embodiment

FIGS. 5A and 5B illustrate a safety cabinet according to a third embodiment of the present invention. FIG. 5A is a side sectional structural view illustrating a safety cabinet during working of the third embodiment, and FIG. 5B is an example of a cross-sectional front view illustrating the safety cabinet during working of the third embodiment.

In the third embodiment, a photoelectric sensor 121a is provided in the measurement probe 116, and a photoelectric sensor light-receiving unit or reflecting unit 121b is provided in the opposing workspace wall surface 106a in comparison with FIGS. 2A and 2B of the first embodiment.

The user places the measurement probe 116 at an appropriate position which reacts with the dust 114 scattering at the time of work. At the time of work, since the hand 119 is inserted between the photoelectric sensor 121a and the photoelectric sensor light-receiving unit or reflecting unit 121b, it is possible to determine that the work is in progress by the reaction of the photoelectric sensor 121a with the hand 119.

According to the present embodiment, since the photoelectric sensor and the photoelectric sensor light-receiving unit or the reflecting unit are provided, it is possible to detect whether the user performs the work, and to detect the work time or non-work time.

Fourth Embodiment

FIGS. 6A and 6B illustrate a safety cabinet according to a fourth embodiment of the present invention. FIG. 6A is a side sectional structural view illustrating the safety cabinet of the fourth embodiment, and FIG. 6B is an example of an external front view illustrating the safety cabinet of the fourth embodiment.

In the fourth embodiment, the photoelectric sensor 121a is provided on the left side of the working opening portion 104 and the photoelectric sensor light-receiving unit or reflecting unit 121b is provided on the right side of the working opening portion 104 in comparison with FIGS. 2A and 2B of the first embodiment. The arrangement on the left and right may be opposite.

The user places the measurement probe 116 at an appropriate position which reacts with the dust 114 scattering at the time of work. At the time of work, the hand 119 is always inserted into the workspace 106 from the working opening portion 104. It is possible to determine that the working is in progress when the light of the photoelectric sensor 121a is shielded by the hand 119.

When the dust 114 generated in the workspace 106 is detected by the measurement probe 116, the place in which the dust 114 is generated needs to be on windward closer to the rectifying plate 110 than the measurement probe 116. There is little possibility that the dust 114 flows to an upstream side against the flow of air flow. In the fourth embodiment, by setting the height position of the measurement probe 116 from the workbench 107 to be equal to or lower than the height of the photoelectric sensor 121a from the workbench 107, it is possible to reliably capture the dust 114 generated at the time of work by the hand 119 with the measurement probe 116. The photoelectric sensor 121a of the working opening portion 104 may be provided with two pairs or three pairs instead of a pair to detect various heights of the hand 119.

According to the present embodiment, since the photoelectric sensor is provided on either the right side or the left side of the working opening portion and the photoelectric sensor light-receiving unit or reflecting unit is provided on the other side thereof, it is possible to detect whether the user is working and to detect the work time or non-work time.

Figure 7:
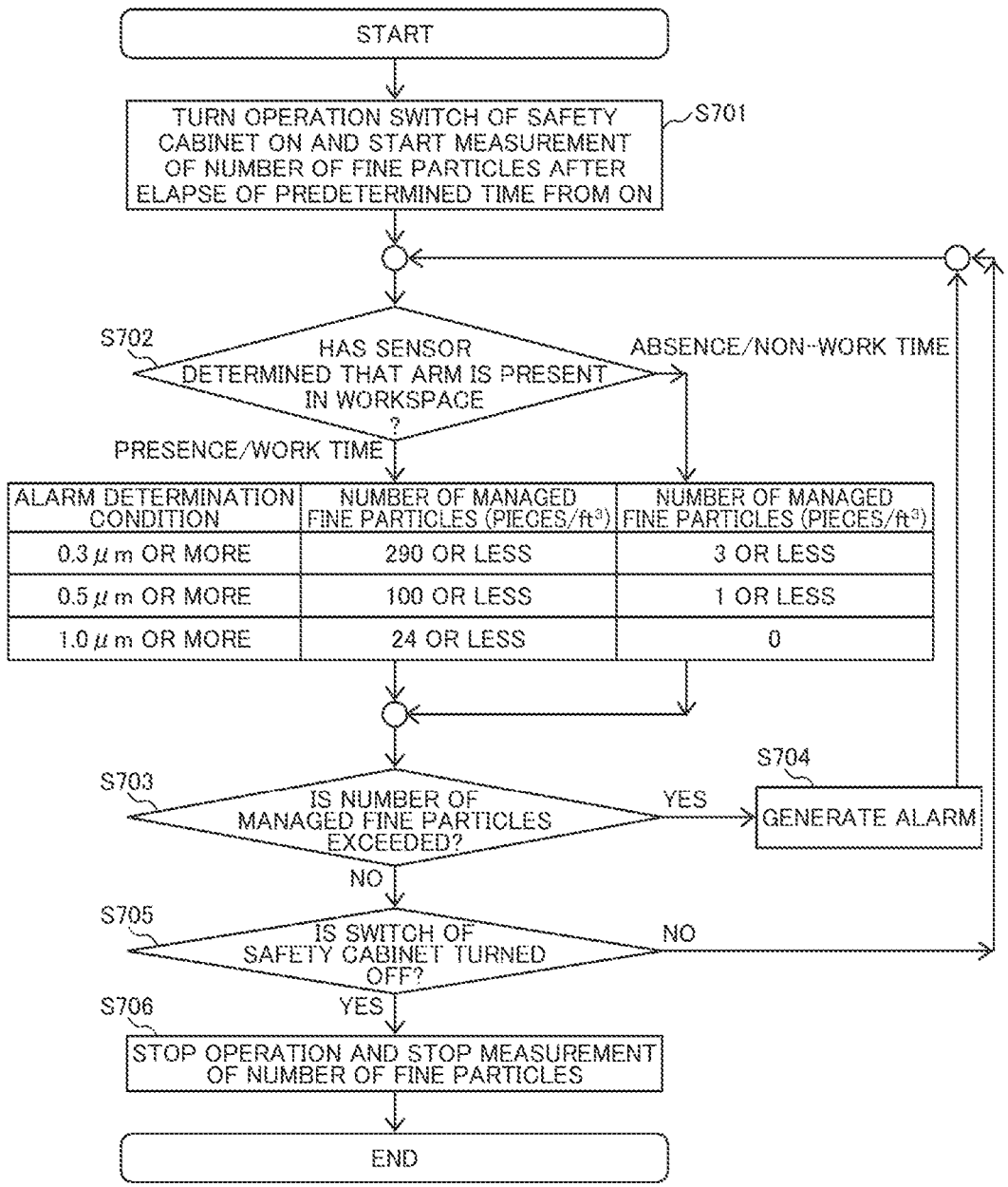
FIG. 7 is an example of an operation flowchart of the safety cabinet of the second to fourth embodiments.

FIG. 7 illustrates an example of an operation flowchart of the safety cabinet of the second to fourth embodiments.

The operation switch of the safety cabinet is turned on (S701). The cleaned air 102 blows out into the workspace 106 of the safety cabinet 100 and the concentration of the fine particles in the workspace 106 decreases. However, since the concentration of fine particles dose not decrease immediately after the operation switch of the safety cabinet is turned on, measurement of the number of fine particles is started by the particle counter 117 after a predetermined time elapses from on.

When the working is performed in the workspace 106 of the safety cabinet 100, the sensors such as the proximity sensor 120 and the photoelectric sensor 121a react with the hand 119 to determine that the working is in progress (S702). When the hand 119 is determined to be present, determination is made with the number of the managed fine particles at the time of work, and when it is determined that there is no hand 119, determination is made with the number of the managed fine particles at the time of non-work (S703). Other operations are the same as the operation flowchart of FIG. 3A of the first embodiment.

Fifth Embodiment

Figure 8:
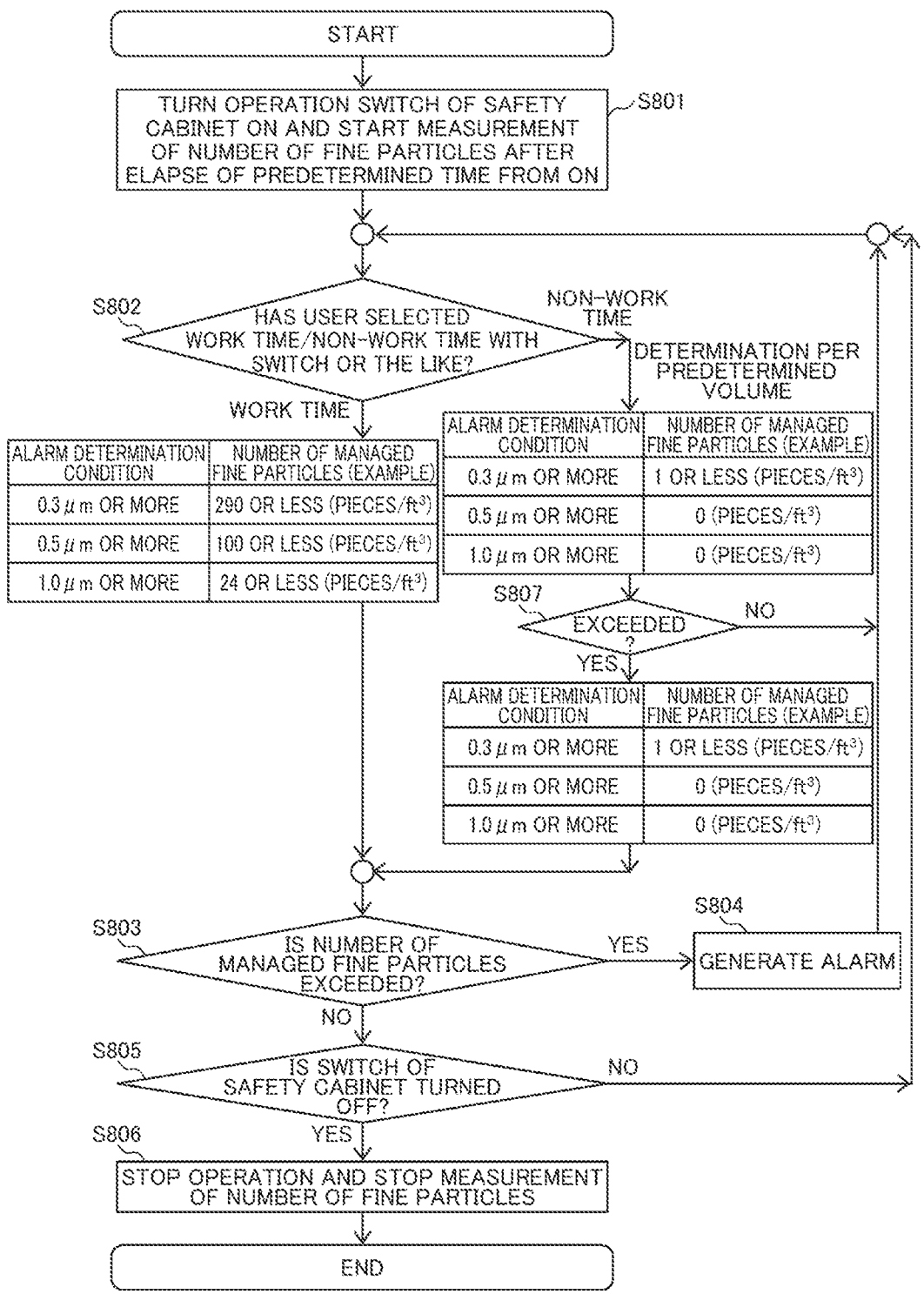
FIG. 8 is an example of an operational flowchart of a safety cabinet of a fifth embodiment.

FIG. 8 illustrates an example of an operational flowchart of the safety cabinet of the fifth embodiment of the present invention.

The operation flowchart of FIG. 8 differs from the operation flowcharts of FIGS. 3 and 7 in the alarm determination method at the time of non-work.

When the number of the managed fine particles per unit volume at the time of non-work is set as a small number such as 1 (pieces/ft$^3$) or 0 (pieces/ft$^3$), there is a possibility that the dust 114 adhering to the sampling tube 117 scatters due to vibration or the like, and the particle counter 117 measures the scattered dust. Alarm issued by warning at this time is not a correct operation. In order to prevent this, the following operational flowchart is adopted.

A particle of 0.5 μm or more at the time of non-work will be described as an example. When the air in the workspace 106 of a predetermined volume, for example 1 ft$^3$ (28.3 liters), is sampled from the measurement probe 116 and the particle counter 117 counts 1 piece/ft$^3$, the number of the managed fine particles of 0 (pieces/ft$^3$) or more is obtained. However, in the first time, it is not determined that the alarm warning is necessary (S807). Subsequently, when the air in the workspace 106 of 1 ft$^3$ (28.3 liters) is sampled and the particle counter 117 measures 1 piece/ft$^3$, since the number of managed fine particles of 0 (pieces/ft$^3$) or more is obtained, it is determined that the particles exceed the managed fine particles (S803), and an alarm is issued by warning (S804). Although the number of times of sampling for determining excess of the number of fine particles is twice in FIG. 8, it may be two or more times. The other operation flowcharts are the same as the operation flowcharts of FIG. 3 and FIG. 7.

According to the present embodiment, when the number of fine particles of the determination condition is small, even when dust adhering to the measurement probe 116 and the sampling tube 118 is sucked into the particle counter 117, it is possible to monitor an appropriate environment without alarm by warning.

Sixth Embodiment

Figure 9:
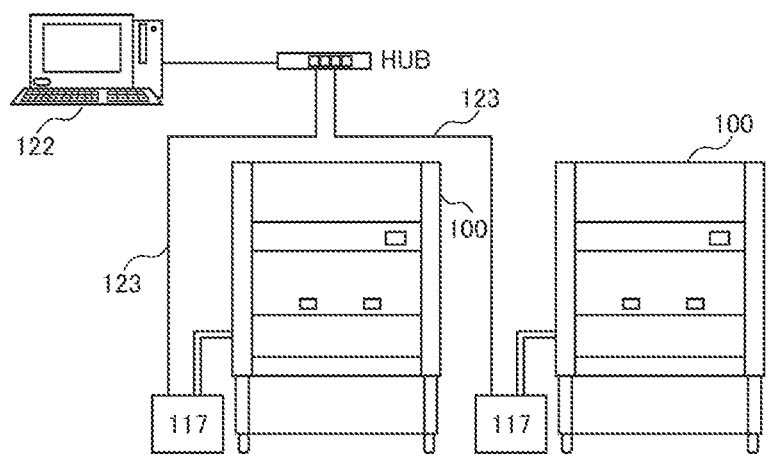
FIG. 9 is an example of a system configuration diagram illustrating a safety cabinet according to a sixth embodiment.

FIG. 9 illustrates an example of a system configuration diagram of a safety cabinet according to a sixth embodiment of the present invention.

A relation between the safety cabinet 100, the measurement probe 116, and the particle counter 117 is the same as those of the first to fifth embodiments. The particle counter 117 measures the number of fine particles (pieces/ft$^3$) of several kinds of particle sizes. The particle counter 117 can output the number of fine particles measured by communication means 123 to a host device 122. Upon receipt of the number of fine particles having several kinds of particle sizes, the host device 122 makes determination on the number of managed fine particles of each particle size illustrated in FIGS. 3, 7, and 8. Since the particle counter 117 only outputs the number of fine particles, a plurality of safety cabinets 100 and the particle counter 117 are connected to the host device 122, each particle counter 117 is addressed, and the number of fine particles of each particle counter 117 may be determined by the host device on the basis of the number of managed fine particles.

According to the present embodiment, since the cleanliness is collectively determined by the host device on the basis of the number of fine particles measured by the plurality of particle counters, there is no need to individually provide the cleanliness determination device.

Seventh Embodiment

Figure 10A:
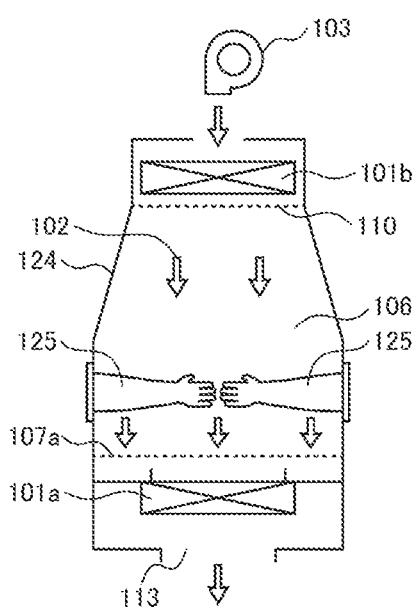
FIG. 10A is a side sectional structural view illustrating an isolator according to a seventh embodiment of the present invention.
Figure 10B:
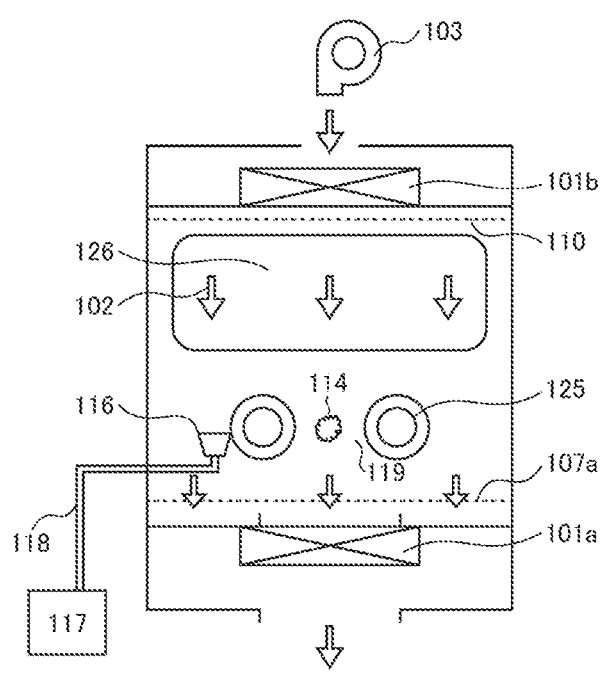
FIG. 10B is an example of a cross-sectional front view illustrating the isolator according to the seventh embodiment.

FIGS. 10A and 10B illustrate an isolator according to a seventh embodiment of the present invention. FIG. 10A is a side sectional structural view of the isolator of the seventh embodiment, and FIG. 10B is an example of a cross-sectional plan view of the isolator of the seventh embodiment. In the seventh embodiment, the present invention is applied to an isolator.

An isolator 124 is a hermetically-sealed workspace 106 except for the portions of the blowing HEPA filter 101b and the exhaust HEPA filter 101a through which the air flows.

The air from which the dust is removed and which is blown out from the blowing HEPA filter 101b is rectified by the rectifying plate 110, and is blown out into the workspace 106 as the cleaned air 102. The worker conducts experiments in the cleaned workspace 106. When a sample is taken in and out of the workspace 106, the sample is delivered from a decontamination pass box (not illustrated) that decontaminates the sample at the time of delivery. The worker inserts the hand 119 into a globe 125 provided on the wall surface of the isolator 124 and performs the experimental work, while viewing the interior of the workspace 106 through a viewing window 126. The air in the workspace 106 passes through an opening portion formed in the working surface 107a through which air passes, and the dust 114 containing aerosol and bacteria is removed by the exhaust HEPA filter 101a, and the air is exhausted from the exhaust port 113 to the outside of the isolator 124.

The measurement probe 116 is disposed in the workspace 106 of the isolator 124. The measurement probe 116 is connected to the particle counter 117 by a sampling tube 118. The operation of taking in the air in the workspace 106 by the measurement probe 116 and determining the number of managed fine particles at the time of work and non-work by the particle counter 117 is the same as that of the first to sixth embodiments.

In the first to seventh embodiments, the management method of the number of fine particles equivalent to the cleanliness class 5 in JIS B 9920 "evaluation method of air cleanliness of clean room" has been described, even if the number of fine particles having different levels such as cleanliness class 4 and class 3 is adopted, the method of determining the alarm is the same. Table 2 shows the upper limit concentration (piece/m$^3$) in the case of class 3 and class 4.

TABLE 2

Upper limit concentration of representative cleanliness of JIS B 9920 "evaluation method of air cleanliness of clean room"

| Cleanliness class | Upper limit concentration (pieces/m$^3$) Measurement particle size | | | | | |
|---|---|---|---|---|---|---|
| | 0.1 μm or more | 0.2 μm or more | 0.3 μm or more | 0.5 μm or more | 1 μm or more | 5 μm or more |
| Class 3 | 1,000 | 237 | 102 | 35 | 8 | |
| Class 4 | 10,000 | 2,370 | 1,020 | 352 | 83 | |
| Class 5 | 100,000 | 23,700 | 10,200 | 3,520 | 832 | 29 |

In each of the above embodiments, the air in the workspace 106 is sucked by the particle counter 117 for the purpose of managing prevention of mixing of general bacteria or the like in the producing process of sterile medicinal products. However, when the management at the time of work of this embodiment is applied to the case of handling a certain infectious material which is the main purpose of the safety cabinet 100, since the particle counter 117 may be contaminated with infectious material, attention should be taken.

The example in which the present invention is applied to a safety cabinet is described in the first to sixth embodiments, the example in which the present invention is applied to an isolator is described in the seventh embodiment, but the present invention is applicable to an isolation device such as a safety cabinet, a clean bench, an isolator, and a clean booth.

REFERENCE SIGNS LIST

100 Safety cabinet
101a Exhaust HEPA filter
101b Blowing HEPA filter
102 Cleaned air
103 Blower
104 Working opening portion
105 Front shutter
106 Workspace
106a Workspace wall surface
107 Workbench
107a Working surface
108 Workbench front suction port
109 Rear suction port
110 Rectifying plate
111 Rear flow path
112 Pressure chamber
113 Exhaust port
114 Dust (containing aerosol and bacteria)
115 Inflow air flow
116 Measurement probe
117 Particle counter
118 Sampling tube
119 Hand
120 Proximity sensor
121a Photoelectric Sensor
121b Photoelectric sensor light-receiving unit or reflecting unit
122 Host unit
123 Communication means
124 Isolator
125 Glove
126 Viewing window
201 Particle counter
202 Storage unit
203 Switch or sensor
204 Selection unit
205 Cleanliness determination unit
206 Alarm generation unit (output unit)

The invention claimed is:

1. An isolation device with built-in particle counter which supplies cleaned air with dust filtered by air cleaning means to a workspace, the isolation device comprising:

a measurement probe for air intake disposed in the workspace;

a particle counter which measures and outputs a number of fine particles having a plurality of particle sizes of air in the workspace taken in by the measurement probe;

a storage unit which stores a number of managed fine particles for each of the plurality of particle sizes, the number of managed fine particles being determined in number of fine particles per unit volume and divided into a work time and a non-work time;

a cleanliness determination unit which compares the number of fine particles having the plurality of particle sizes measured by the particle counter with the number of managed fine particles having the plurality of particle sizes stored in the storage unit to determine cleanliness; and an output unit which outputs an alarm when the number of fine particles in the workspace during operation is determined to be greater than the number of the managed fine particles for any of the plurality of particle sizes, and for each of the work time or the non-work time in the cleanliness determination unit.

2. The isolation device with built-in particle counter according to claim 1, further comprising:

a selection unit which selects the number of managed fine particles in the storage unit, depending on the work time and the non-work time, wherein the cleanliness determination unit compares the number of the managed fine particles at the selected work time or the non-work time with the number of the measured fine particles.

3. The isolation device with built-in particle counter according to claim 2, further comprising:

a sensor which detects presence or absence of a worker's hand in the workspace, wherein the selection unit selects the number of managed fine particles at the time of work or non-work, on the basis of the output of the sensor.

4. The isolation device with built-in particle counter according to claim 1, wherein a suction port of the measurement probe is disposed in a direction in which the cleaned air is blown out, and a difference between a blowing speed of the cleaned air and a sucking speed of the measurement probe is managed within ±20%.

5. The isolation device with built-in particle counter according to claim 1, wherein the isolation device with built-in particle counter is a safety cabinet or an isolator.

* * * * *